United States Patent [19]

Michon et al.

[11] Patent Number: 5,057,682
[45] Date of Patent: Oct. 15, 1991

[54] QUIESCENT SIGNAL COMPENSATED PHOTODETECTOR SYSTEM FOR LARGE DYNAMIC RANGE AND HIGH LINEARITY

[75] Inventors: Gerald J. Michon, Waterford; Dale M. Brown, Schenectady, both of N.Y.

[73] Assignee: General Electric Company, Schenectady, N.Y.

[21] Appl. No.: 607,222

[22] Filed: Nov. 5, 1990

Related U.S. Application Data

[63] Continuation-in-part of Ser. No. 456,903, Dec. 26, 1989, abandoned.

[51] Int. Cl.[5] ............................................. H01J 40/14
[52] U.S. Cl. ............................... 250/214 C; 307/311
[58] Field of Search ............ 250/214 A, 214 C, 214 R, 250/208.2; 307/311

[56] References Cited

U.S. PATENT DOCUMENTS

| | | | |
|---|---|---|---|
| 3,877,039 | 4/1975 | Ichinohe et al. | 354/24 |
| 4,437,743 | 3/1984 | Sakai et al. | 354/402 |
| 4,659,930 | 4/1987 | Johnson et al. | 307/311 |
| 4,781,195 | 11/1988 | Martin | 128/633 |
| 4,806,748 | 2/1989 | Takami et al. | 250/214 C |
| 4,857,725 | 8/1989 | Goodnough et al. | 250/214 A |

*Primary Examiner*—David C. Nelms
*Attorney, Agent, or Firm*—Marvin Snyder; James C. Davis, Jr.

[57] ABSTRACT

The linearity and dynamic range of a photodetector system is enhanced by providing real time cancellation of condition-dependent quiescent output signals from the photosensitive devices by provision of a condition-dependent output signal monitoring device which drives the input section of a current mirror having output sections connected to the active photosensitive devices to zero out the condition-dependent quiescent output signals of those photosensitive devices during system operation. Multiple output sections may be run from a single input section of the current mirror.

30 Claims, 4 Drawing Sheets fig. 1 fig. 2 fig. 3 fig. 4

QUIESCENT SIGNAL COMPENSATED PHOTODETECTOR SYSTEM FOR LARGE DYNAMIC RANGE AND HIGH LINEARITY

This application is a continuation-in-part, of application Ser. No. 07/456,903, filed 12/26/89, now abandoned.

RELATED APPLICATION

This application is related to application Ser. No. 456,903, filed Dec. 26, 1989 and entitled "Low Capacitance, Large Area Semiconductor Photodetector and Photodetector System" by D. M. Brown et al. This application is incorporated herein by reference.

BACKGROUND OF THE INVENTION

1. Field of the Invention

This invention relates to the field of photodetector systems, and more particularly, to the field of light intensity measuring photodetector systems.

2. Background Information

Some opto-electronic systems such as camera focus determination systems, rely on conversion of an incident optical image to corresponding electrical signals for processing, but do not require quantitative measurement of incident light intensity in order to fulfill their objective. However, such systems may require adjustment or compensation for incident light intensity to prevent saturation of system components or other effects which would prevent proper operation of the system. U.S. Pat. No. 4,437,743 to Sakai et al. discloses such a camera focus adjustment system. That system employs a CCD imager to convert optical focus information to electronic signals for processing to determine the degree of focus of the scene being viewed by the camera. The integration period for the CCD is adjusted in accordance with the incident light intensity. The system compensates for the sensor dark current variations with the length of the integration period by masking a portion of the CCD to obtain a dark current signal which is the first bit read out of the CCD. This value is sampled and held and applied to one input of a differential amplifier while the image signals are applied to the other input of the differential amplifier to provide a so-called dark current compensated signal whose amplitude is then used to adjust the CCD integration time.

Many other electronic systems require quantitative measurement of incident light intensity for their proper operation. Such systems include focal plane imaging systems, exposure setting systems for cameras, medical diagnostic systems such a photoelectric LED blood oxygen monitoring systems and computed tomography (CT) systems employing solid scintillator x-ray detection systems. For example, U.S. Pat. No. 4,781,195 to Martin discloses a blood oxygen monitoring system which measures the ambient light effect on its sensor diodes, fixes a compensation for that ambient light effect and then takes a measurement using that compensation to correct for the ambient light. The ambient light effect is then measured again and a new compensation is established for the next measurement and so forth. Thus, this system alternates measurement and compensation determination cycles. U.S. Pat. No. 3,877,039 to Ichinohe et al. discloses a camera exposure setting system which first measures an ambient light intensity by charging a capacitor and then subtracts a dark current signal by applying a current to discharge the capacitor as a means of compensating for the non-linearity introduced by its photosensitive diodes. U.S. Pat. No. 4,857,725 to Goodnough et al. discloses a diode-based focal plane imaging system which determines a compensation for the difference in the photoresponses of each associated pair of diodes and maintains that compensation over a measurement interval which is preferably an entire mission.

In a computed tomography (CT) x-ray scanning system which employs a solid, luminescent scintillator to convert incident x-rays to luminescent light a multicellular x-ray scintillation detector system is used to convert the incident x-ray intensity to electrical signals whose amplitudes are measures of the x-ray intensity. Such CT scanning systems include a gantry on which an x-ray source is mounted on one side of a measurement zone and an x-ray scintillation detector system is mounted on the opposite side of the measurement zone in alignment with the x-ray beam. Such systems preferably employ a fan-shaped x-ray beam and a scintillation x-ray detector which may comprise 1,000 or more separate detection cells disposed in a linear array.

For maximum data collection accuracy, the individual cells of the scintillator detection system are disposed immediately adjacent to each other, thereby maximizing the collection by the scintillation detector system of the x-rays emerging from the patient or other object being examined. The individual blocks of scintillator material may typically be about 1 mm wide by about 30 mm high by about 3 mm deep. The width of the scintillator block being determined by the desired data resolution in the direction of the length of the scintillation detector array, the height of the block being determined by the thickness of the x-ray fan beam in combination with the desired vertical thickness of the measurement zone and the depth of the scintillator block being determined by the x-ray stopping power of that block.

For ease of manufacture and assembly, it is preferred to have the photoresponsive diodes associated with a number of adjacent scintillator blocks integrated in a single chip or wafer of semiconductor material. The patterned side of the semiconductor structure and the electrodes thereon are disposed toward the blocks of scintillator material for maximum conversion of luminescent light to electrical signals. The immediate side-by-side placement of adjacent scintillation detector cells requires that the output connections to the individual diodes be located adjacent a narrow end of the diode in order that wires, conductors and other optical obstructions may be excluded from the active collection area of the diode to maximize light collection, system efficiency and cell-to-cell uniformity within the detector system.

To generate a computed tomography image, the gantry is rotated about the measurement zone while the x-ray beam is on and the output from the scintillation detector system is recorded or stored for concurrent or subsequent processing. Data is taken continuously during each revolution of the gantry. At each position where data is taken, the output of each of the detector cells is determined and stored.

In such a system, the vast quantity of data which has been recorded ($\sim 4 \times 10^5$ data points) is subsequently processed to generate an image of the object or patient disposed in the measurement zone during the measurement process.

Each data point comprises the position of the detection cell at the time the data was taken and the amplitude of the output from the photodiode associated with that cell at that time. All of these output amplitudes are processed using computerized tomography image reconstruction techniques, which are known in the art, to generate an image of the object in the measurement zone. The accuracy of the generated image depends on the accuracy with which incident x-ray intensity on the scintillator cell is converted to an electronic signal having an amplitude which is a measure of that x-ray intensity.

Thus, image accuracy is limited by the ability of the scintillation x-ray detection system to accurately convert x-ray intensity to electronic signal amplitude. In order to maximize throughput, minimize patient x-ray exposure and inconvenience, it is considered desirable to perform a data collection scan as rapidly as possible. In order to provide accurate image generation with low intensity x-rays and high scan rates, it is necessary that the photodetection system accurately transduce incident luminescent light intensity to a corresponding electrical signal amplitude in a linear manner across a wide dynamic range including both very low and very high light intensities, a dynamic range of $10^4$ to $10^5$ or more being considered desirable.

Because of this wide desired dynamic range and the desire to be able to operate at very small rates of photo generated charge carriers (in order to minimize patient exposure to x-rays), it is necessary to minimize noise contributions to signals throughout the overall data acquisition system.

Present General Electric Company CT scanners of the Zeus type employ a solid ceramic scintillator to convert incident x-ray intensity to luminescent light. A large area PIN photosensitive diode on the order of $\frac{3}{4}$ mm $\times$ 30 mm in area is optically coupled to the scintillator block and detects the luminescent light produced thereby and converts that light to an output current whose amplitude is linearly related to the intensity of the luminescent light and thus to the incident x-ray intensity, provided the scintillator provides a linear x-ray-to-luminescent-light conversion. This output current is in turn converted to an output voltage by an operational amplifier which is dedicated to that photosensitive diode.

Many design considerations go into the design of the photodetector diode and its operational amplifier output system. For accurate image generation, each of the scintillator detector cells must provide substantially identical conversion of x-ray intensity to electronic signal amplitude. Consequently, it is necessary to minimize offset voltages among the operational amplifiers connected to the various photodetector diodes. This is facilitated by operating the diode in a zero bias (photoconductive) mode to minimize offset voltages and thermal drift.

Data is taken substantially continuously during a scan. That is, the output from the photosensitive diodes is continuous, as is the output from the operational amplifiers to which the diodes are connected. The output from the operational amplifiers is sampled by analog-to-digital conversion and stored at the desired data acquisition rate to provide data at each of the desired positions of the scanning gantry.

In order to produce a clear, high quality image of the object or patient being scanned, such a CT scanning system requires that the electrical output signal be directly proportional to the luminescent light intensity. Any deviation from such direct proportionality constitutes system noise which degrades the obtainable image quality. As is well known in the semiconductor art, the response characteristics of a photosensitive diode depend on the diode's temperature because of an increase in the inherent internal generation of hole-electron pairs within the semiconductor material with increasing temperature. Such internally generated thermal hole-electron pairs are indistinguishable to the overall system from the hole-electron pairs which are generated by the incident luminescent light which it is desired to measure. Thus, it is important to stabilize the diode temperature and thermal generation rate. Consequently, the photodiodes are thermally coupled to a heat sink which is heated to above ambient temperature in order that the temperature of the diodes may be closely controlled. During the course of a scan, the photosensitive diodes heat up as a result of the energy dissipated within the diodes during the scan interval. The resulting increase in temperature produces an increase in the output current for the photodiode for a fixed incident luminescent light intensity. To compensate for this change, the temperature of the diodes is measured before the beginning of a scan and at the end of the scan and the data acquired during that scan is compensated by subtracting a compensation signal from each data value. The compensation signal is determined on the basis of a linear increase in temperature during the scan period in combination with the scan time at which the data was taken.

With the desire for further increases in system linearity and decreases in system noise, improved photodetector temperature, linearity and noise control is needed.

OBJECTS OF THE INVENTION

Accordingly, a primary object of the present invention is to provide improved linearity and decreased noise in a photodetector system.

Another object of the present invention is to continuously compensate a photodetector system for condition-dependent sensor device characteristics.

Another object of the present invention is to compensate a plurality of photosensitive devices for their condition-dependent characteristics in an efficient, minimum circuitry manner.

Another object of the present invention is to compensate a plurality of devices of different sizes for their condition-dependent characteristics based on the condition-dependent response of one device.

SUMMARY OF THE INVENTION

The above and other objects which will become apparent from the specification as a whole, including the drawings, are accomplished in accordance with one embodiment of the present invention by providing a condition-dependent quiescent-output-signal monitoring device which is shielded from luminescent light, but otherwise disposed in the same environment as, and preferably integrated with, the photosensitive device. The condition-dependent quiescent output signal from this monitor device drives the input section of a current mirror whose output section is coupled to the active photosensitive device to subtract a corresponding condition-dependent quiescent output signal from the output signal of the active photosensitive device before that output signal is applied to the operational amplifier to which the active device is coupled. In this manner, the quiescent output signal of the active photosensitive device is continuously cancelled in real time prior to amplification thereof. This makes the entire dynamic range of the operational amplifier available for the luminescent output signal from the photosensitive device, eliminates extrapolation errors and simplifies the data reduction process by eliminating the need for subsequent temperature corrections.

For ease of manufacture and assembly, it is preferred to integrate the photosensitive devices for a plurality of x-ray detection cells in a single semiconductor wafer. In accordance with one embodiment of the present invention, a single condition-dependent-quiescent-output-signal monitoring device is provided on each integrated wafer with that device driving the input section of the current mirror with the current mirror having separate output sections for each of the light-responsive photosensitive devices on the wafer. The entire current mirror system is preferably integrated on the wafer. For compactness, the condition-dependent-quiescent-output-signal monitoring device may be made smaller (or larger) than the luminescent active photosensitive devices with the current mirror system providing appropriate scaling to provide accurate compensation of the condition-dependent quiescent output signal of each active photosensitive device. Where the light-receptive photosensitive devices are arranged in a linear array, two or more monitor devices may be provided in spaced apart locations to more accurately respond to the conditions on which the quiescent output signal is dependent with the multiple monitor devices connected in parallel (or another appropriate manner) to combine or average their responses to control the input section of the current mirror.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

DETAILED DESCRIPTION

Figure 1:
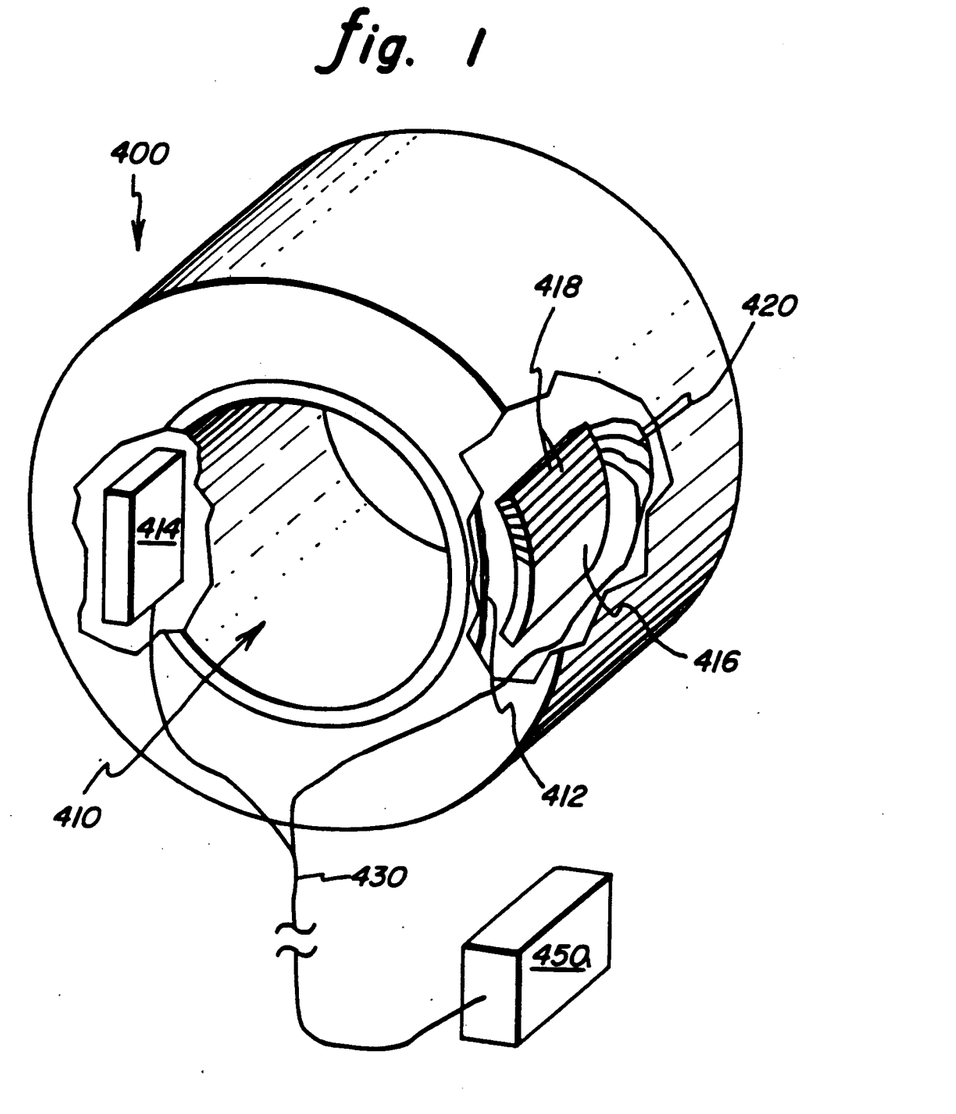
FIG. 1 illustrates in schematic form a portion of a computed tomography machine employing the present invention.

A computed tomography (CT) scanning system 400 is illustrated schematically in FIG. 1. This CT scanning system 400 comprises a cylindrical enclosure 410 in which the patient or object to be scanned or examined is positioned. A gantry 412 surrounds the cylinder 410 and is configured for rotation about the cylinder concentric with the cylinder's axis. The gantry 412 may be designed to revolve for one full revolution and then return or may be designed for continuous rotation, depending on the system used to connect the electronics on the gantry to the rest of the system. The electronics on the gantry include an x-ray source 414 which preferably produces a fan x-ray beam which encompasses a scintillation detector system 416 mounted on the gantry on the opposite side of the cylinder 410. The fan pattern of the x-ray source is disposed in the plane defined by the x-ray source and the scintillation detector system 416. The scintillation detector system 416 is very narrow or thin in the direction perpendicular to the plane of the x-ray fan beam. Each cell 418 of the scintillation detector system 416 incorporates a solid transparent bar of scintillator material and a photodetector diode optically coupled to that scintillator bar. The output from each photodetector diode is connected to an operational amplifier which is mounted on the gantry. The output from each operational amplifier is connected either by individual wires 420 or by other electronics to the main control system 450 for the computed tomography system. In the illustrated embodiment, power for the x-ray source and signals from the scintillation detector are carried to the main control system 450 by a cable 430. The use of the cable 430 generally limits the gantry to a single full revolution before returning to its original position. Alternatively, slip rings or optical or radio transmission may be used to connect the gantry electronics to the main control system 450 where continuous rotation of the gantry is desired. In CT scanning systems of this type, the scintillator material is used to convert incident x-rays to luminescent light which is detected by the photodetector diode and thereby converted to an electrical signal as a means of converting the incident x-rays to electrical signals which may be processed for image extraction and other purposes. At present, one of the limitations on the capabilities of such systems is the characteristics of the photosensitive diodes which convert the luminescent light to electrical signals which are a measure of the intensity of the luminescent light.

Figure 2:
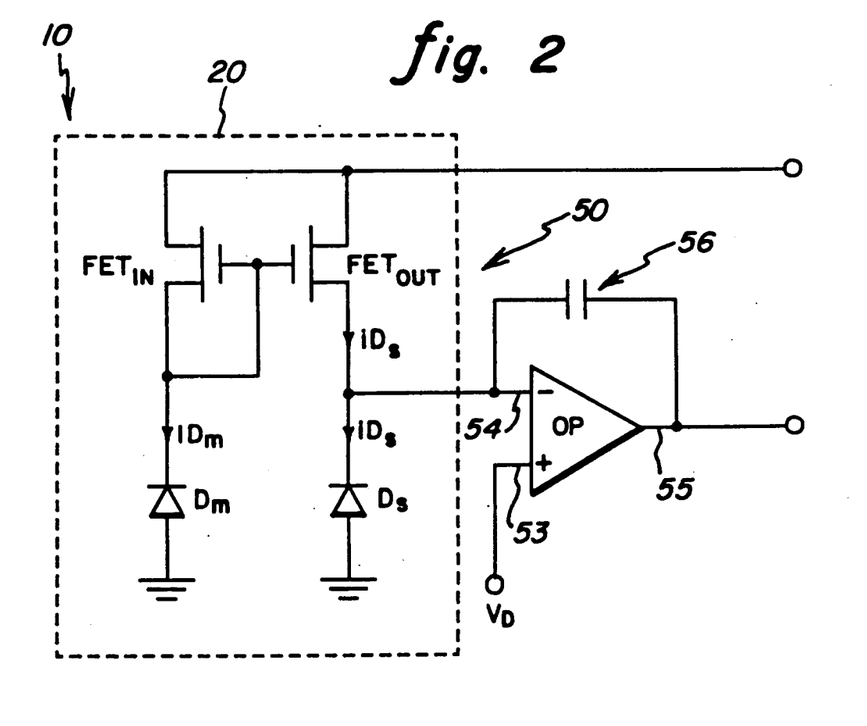
FIG. 2 is a schematic circuit illustration of a photodetector system in accordance with the present invention.

In FIG. 2, a photodetector system in accordance with the present invention is illustrated generally at 10. The system 10 comprises a condition-dependent-quiescent-output-signal monitoring device in the form of a diode $D_m$ which is connected in series with an FET identified as $FET_{in}$ as the input side of a current mirror 20. The source-to-drain current path of $FET_{in}$ is connected in series with the diode $D_m$ between a voltage source $V_D$ and ground so that the current in the diode $D_m$ flows through the main conducting path of $FET_{in}$. This is achieved by connecting the anode of diode $D_m$ to the drain of $FET_{in}$. The anode of the diode $D_m$ is also connected to the gate terminal of $FET_{in}$. Because $FET_{in}$ is a P-channel device, the quiescent output signal of diode $D_m$ tends to drive $FET_{in}$ on. This circuit stabilizes when the voltage at the gate of $FET_{in}$ causes the main current of the $FET_{in}$ to be exactly equal to the quiescent, condition-dependent current of the diode $D_m$. The output section of the current mirror includes a second FET ($FET_{out}$) which is connected in series with an active photosensitive device in the form of a diode $D_s$. The anode of the diode $D_s$ is connected to the drain of $FET_{out}$. $FET_{out}$ has its gate terminal connected to the gate terminal of $FET_{in}$. Thus, the same voltage is applied to $FET_{out}$ as is applied to $FET_{in}$. Consequently, the same current per unit area will flow in $FET_{out}$ as flows in $FET_{in}$ provided the two FETs have the same structure (i.e. threshold voltage, channel on-resistance and so forth). If the diodes $D_m$ and $D_s$ are the same size, then the $FET_{in}$ and $FET_{out}$ are also made the same size in order to make the current mirror output current which flows into the diode $D_s$ equal to the current mirror current drawn by the diode $D_m$. In this manner, the quiescent output signal of the photosensitively active device $D_s$ is cancelled or zeroed out by the current mirror. If the diodes $D_m$ and $D_s$ are different sizes, then the sizes of the FETs are adjusted so that the current mirror output current matches the quiescent current of diode $D_s$.

The diodes $D_m$ and $D_s$ are preferably integrated in a single semiconductor chip and fabricated together in order that their structures which determine their respective condition-dependent quiescent currents will be identical and so that their temperatures and other physical conditions will always be substantially the same. The semiconductor material is preferably silicon, but may be other materials in accordance with the intended use of the finished devices and their operating characteristics when fabricated in a particular semiconductor material. An output circuit 50 for the photosensitive device $D_s$ comprises an operational amplifier 52 having a non-inverting input terminal 53, an inverting input terminal 54 and an output terminal 55. A feedback capacitor 56 is connected between the output terminal 55 and the inverting input terminal 54. The inverting input terminal 54 is also connected to the anode of the photosensitive device $D_s$. In this manner, the operational amplifier output is controlled by the luminescent output signal of device $D_s$. That is, the current mirror output section provides a current path for the condition-dependent quiescent output signal of device $D_s$, thereby leaving only the luminescent output signal to drive the operational amplifier 52. Further, since the output current of the current mirror is fixed by the diode $D_m$, none of the luminescent output signal from the diode $D_s$ is diverted away from the operational amplifier. Consequently the output signal at the output terminal 55 of the operational amplifier accurately tracks the the luminescent output signal. The output signal from the operational amplifier 52 is linearly related to the intensity of the luminescent light generated by the x-rays throughout the scanning process and does not need to be adjusted for changes in conditions during a scan. Typically, this output signal drives an analog-to-digital converter whose output is a digital value which is stored and subsequently used in processing the data collected during a scan to produce a computed tomography image of the object or patient being examined.

To save space or for other reasons, the monitor device $D_m$ may be made substantially smaller than the photosensitive device $D_s$ provided that the $FET_{in}$ and the $FET_{out}$ have a size relationship which results in proper cancellation of the condition-dependent quiescent output signal of the device $D_s$. During circuit design and as part of a self-test or calibration process for such a system, the accuracy of the match between the input and output sections of the current mirror may be checked by shielding the device $D_s$ from any luminescent light and measuring the output of the system at the output terminal 55 of the operational amplifier. For a perfect match, this output will be zero, since only the condition-dependent quiescent output signal is present in the device $D_s$ and that signal flows in the output section of the current mirror rather than in the operational amplifier. Any small deviation from zero may be compensated by storage of that value and subtraction of it from data values. Alternatively, and preferably, during the device fabrication process, the devices may be trimmed to adjust that output to zero to provide "perfect" compensation for the condition-dependent quiescent output signal.

The system 10 of FIG. 2 includes a monitor device which is dedicated to a single photosensitive device. Such duplication of devices is not necessary where more than one photosensitive device is present in a single semiconductor wafer or chip. A modified system 10' shown in FIG. 3, uses a single monitor device $D_m$ to control the condition-dependent quiescent signal compensation for a plurality of photosensitive devices $D_{s1}$, $D_{s2}$, ... $D_{sn}$. The system 10' is similar to the system 10 except for the provision of additional output sections for the current mirror with corresponding photosensitive devices and output circuits. It will be noted that the gate of each of the $FET_{out}$'s is connected to the gate of $FET_{in}$ in FIG. 3. Since, to a first order, the gate of a FET draws no current in a steady dc state, the number of output sections to the current mirror is unlimited. In actuality, limitations exist due to propagation time and miniscule leakage, etc. For the active photosensitive devices of the size used in the Zeus CT scanning system, a more realistic limit is the number of active photosensitive devices which may be provided on a single semiconductor wafer in an efficient manner. In particular, 16 active devices is a preferred number to integrate on a single wafer or chip. In such a multiple active device structure, it may be considered desirable to make the monitor device smaller than the active devices in order to save space on the chip or wafer, since the active devices are substantially larger than the various $FET_{out}$'s and the output circuits associated therewith. Consequently, shrinking the monitor device can save substantial semiconductor area. Further, in other applications, the active devices may have a variety of sizes with each active device having an associated $FET_{out}$ which is sized to properly scale the current mirror output signal for that active device to properly compensate its condition dependent quiescent output signal.

Figure 3:
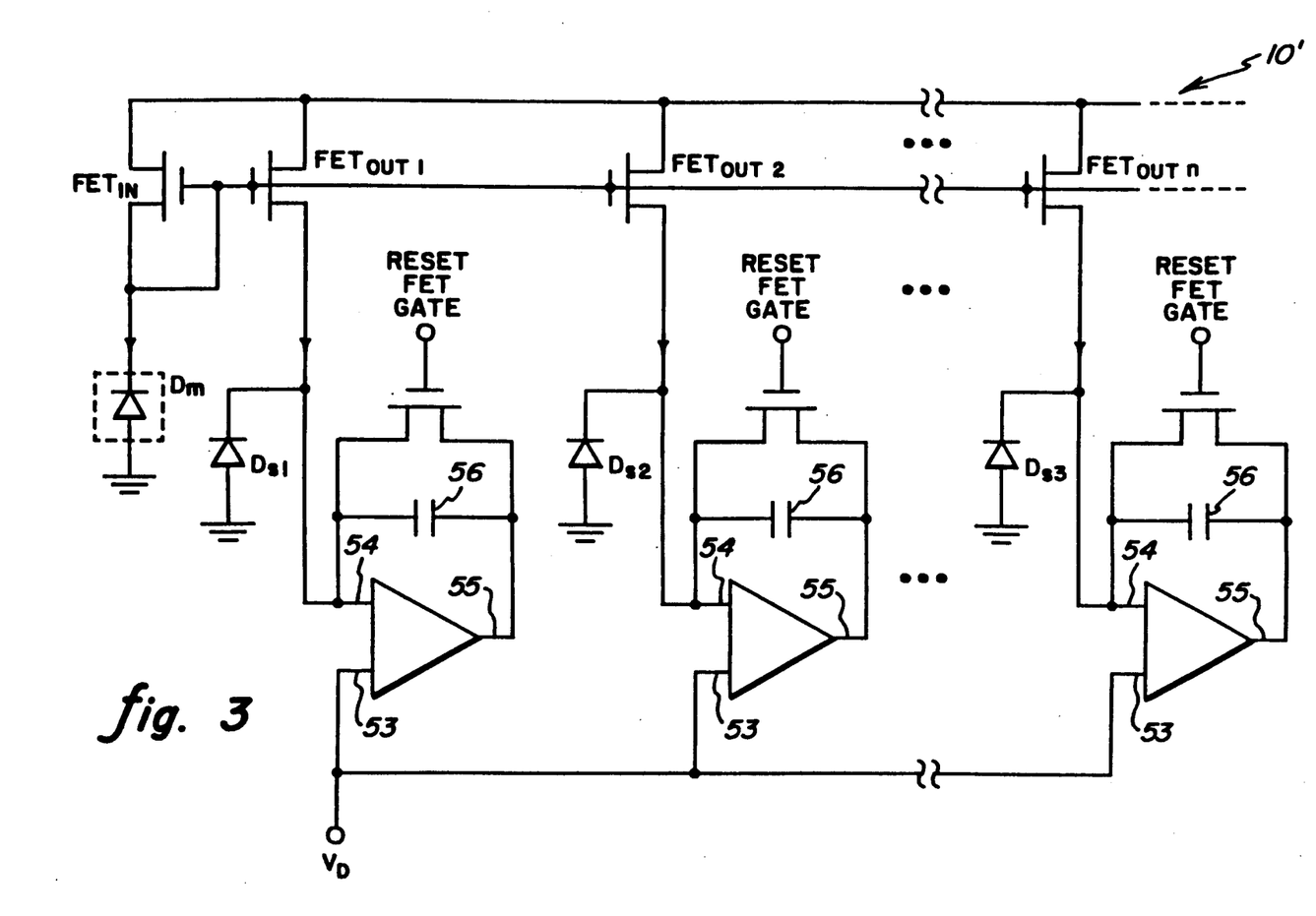
FIG. 3 is a schematic circuit diagram illustration of an embodiment of the present invention in which the current mirror has multiple outputs.

With a system of the type shown in FIG. 3 which includes 16 active luminescent receptive devices, trimming of the current mirror output sections may be particularly advantageous to ensure that each of the x-ray detection cells shares a common response characteristic and to save the processing involved in subtracting offset values from each of the generally 1,000 or more output signals for each measurement position of the scanning gantry.

Figure 4:
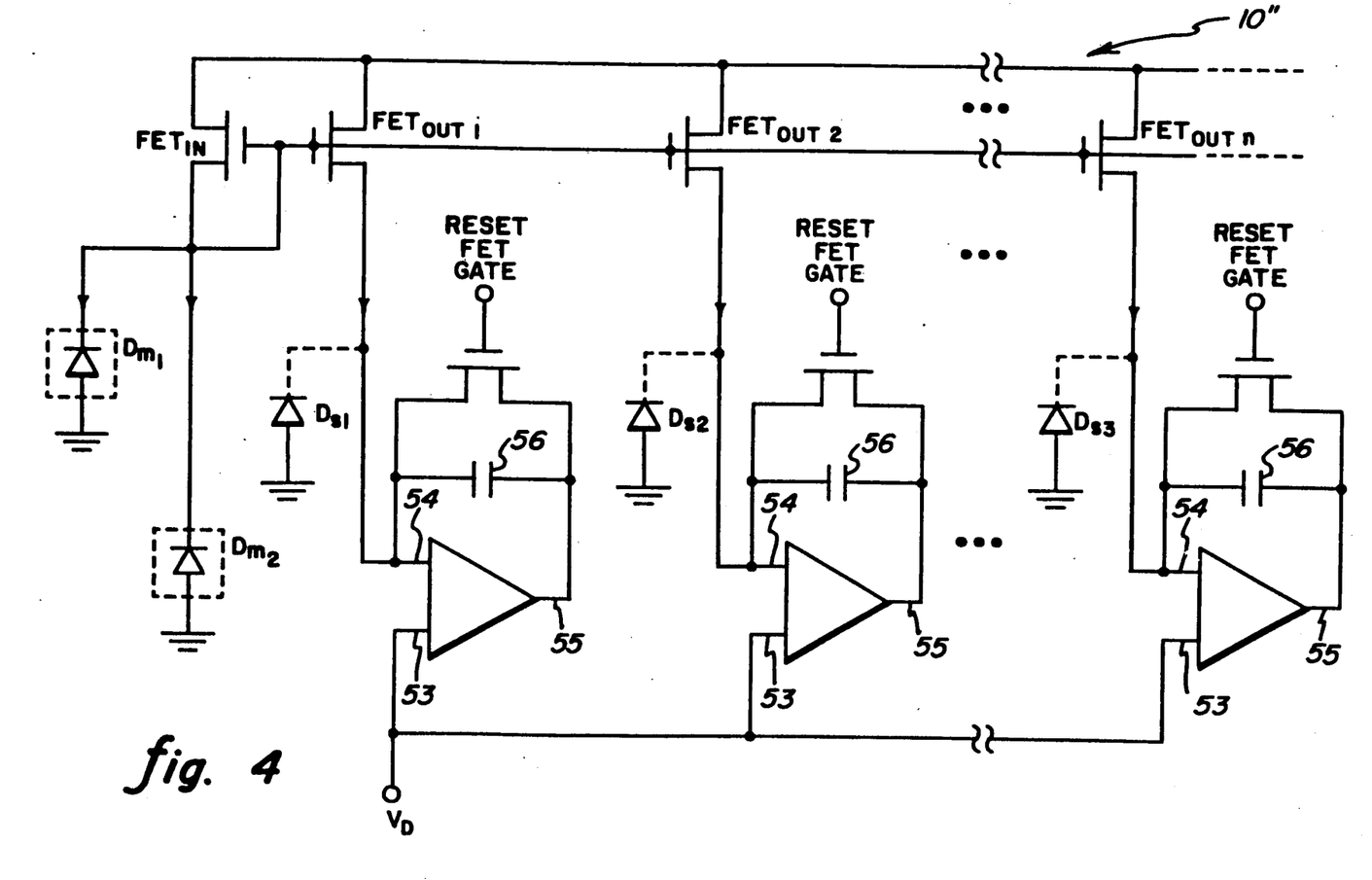
FIG. 4 is a schematic circuit diagram illustration of a modified FIG. 3 embodiment in which a plurality of monitor devices are employed.

In FIG. 4, a modified version 10" of the circuit 10' is illustrated. In this circuit, two separate monitor devices $D_{m1}$ and $D_{m2}$ are connected in parallel in the input section of the current mirror. These separate monitor devices may be positioned at opposite ends of a linear array of active photosensitive devices (actually the 16 element subarray disposed on the chip), may be positioned at opposite sides (top to bottom in the figure) of the array, or in any other desired arrangement. More than two monitor devices may be employed such as one at each end of a subarray and one in the middle, or any other appropriate location which is found to enhance the accuracy of the compensation of the condition-dependent quiescent output signal of the various active devices $D_s$ in that subarray.

Thus, in accordance with the present invention, the condition-dependent quiescent output signal from each active photosensitive device is compensated for in a continuously varying, real time manner, thereby minimizing noise contributions to the overall data acquisition system which result from the temperature or other dependencies of the condition-dependent quiescent output signal. Further, this compensation enhances the linearity of the system by zeroing out this non-luminescent signal which would otherwise add to the luminescent signal and render it non-linear for low incident light intensities with their corresponding low luminescent output signal.

Further, this system avoids the assumption (which is known to be inaccurate in the desired application of this system) that conditions in the measurement system do not change during the measurement interval.

In a CT scanning system of this type, the active photosensitive devices are substantially shielded from the x-rays by the ceramic scintillator material which absorbs upwards of 95% of the x-rays. Where the structure of the monitor device is such that the device is subject to x-ray damage, it may be considered desirable to shield the monitor device from the x-rays by inclusion of a scintillator block between the monitor device and the x-ray source while shielding the monitor device from any luminescent light produced by that scintillator block. In this manner, the condition-dependent quiescent output signal from the monitor device should track with that from the active photosensitive devices over the life of the system.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

What is claimed is:

1. A photodetector system comprising:
   a plurality of photosensitive devices which exhibit a condition-dependent quiescent output signal;
   a plurality of output circuits each connected to receive the output signal from a different one of said photosensitive devices;
   a quiescent signal monitor device having a condition-dependent quiescent output signal which is proportional to that of said photosensitive devices;
   means for shielding said monitor device from the light to be sensed by said photosensitive devices, whereby the output signal from said monitor device is proportional to the condition-dependent-quiescent-output-signal contributions to the output signals of said photosensitive devices;
   current mirror means responsive to the output signal from said monitor device for applying quiescent output signal compensating signals to a plurality of said output circuits to compensate for the condition-dependent-quiescent-output-signal contribution to the output signal of each of said photosensitive devices, whereby the output from each of said output circuits is substantially independent of the condition-dependent quiescent output signal of the one of said photosensitive devices to which it is coupled.

2. The photodetector system recited in claim 1 said photosensitive devices are continuous output
   said photosensitive devices are continuous output devices.

3. The photodetector system recited in claim 2 wherein:
   said quiescent signal is a current.

4. The photodetector system recited in claim 1 wherein:
   said monitor device is a different size than at least some of said photosensitive devices; and
   said current mirror means scales the signal applied to said output circuits in accordance with the relative sizes of said monitor device and said photosensitive devices.

5. The photodetector system recited in claim 4 wherein:
   said quiescent signal is a current.

6. The photodetector system recited in claim 1 wherein:
   said monitor device is a different size than at least some of said photosensitive devices;
   not all of said photosensitive devices are the same size; and
   said current mirror means scales the signal applied to said output circuits in accordance with the relative sizes of said monitor device and said photosensitive devices.

7. The photodetector system recited in claim 6 wherein:
   said quiescent signal is a current.

8. The photodetector system recited in claim 1 further comprising:
   a second monitor device coupled to said current mirror means in a manner to combine the condition-dependent quiescent output signals derived from the first recited and said second monitor devices to more accurately compensate said photosensitive devices of said photodetector system.

9. The photodetector system recited in claim 8 wherein:
   said photosensitive devices are arranged in a linear array extending in a first direction and said monitor devices are disposed on opposite sides of said linear array in a second direction disposed at an angle to said first direction.

10. The photodetector system recited in claim 8 wherein:
    said photosensitive devices are arranged in a linear array extending in a first direction and said monitor devices are spaced apart and disposed in the vicinity of opposite ends of said linear array.

11. The photodetector system recited in claim 10
    said monitor devices are disposed on opposite sides of said linear array in a second direction disposed at an angle to said first direction.

12. A photodetector system comprising:
    a photosensitive device which exhibits a condition-dependent quiescent output signal;
    an output circuit connected to receive the output signal from said photosensitive device;
    a quiescent output signal monitor device having a condition-dependent-quiescent-output-signal response which is proportional to that of said photosensitive device;
    means for shielding said monitor device from the light to be sensed by said photosensitive device, whereby the output signal from said monitor device is proportional to the condition-dependent-quiescent-output-signal contribution to the output signal from said photosensitive device;
    current mirror means responsive to said monitor device for applying a condition-dependent-quiescent-output-signal-compensating signal to said output circuit to compensate for the condition-dependent quiescent output signal from said photosensitive device whereby the output from said output circuit is substantially independent of the condition-dependent quiescent output signal of said photosensitive device.

13. A photodetector system comprising:

a continuous output photosensitive device which exhibits a condition-dependent quiescent current;

an output circuit connected to receive the output current from said photosensitive device;

a quiescent current monitor device having a condition-dependent quiescent current response which is proportional to that of said photosensitive device;

means for shielding said monitor device from the light to be sensed by said photosensitive device, whereby the output of said monitor device is proportional to the condition-dependent quiescent current contribution to the output signal from said photosensitive device;

current mirror means responsive to said monitor device for applying a condition-dependent-quiescent-current-compensating signal to said output circuit to compensate for the condition-dependent quiescent current from said photosensitive device whereby the output from said output circuit is substantially independent of the condition-dependent quiescent current of said photosensitive device.

14. A photodetector system comprising:

a plurality of continuous output photosensitive devices which exhibit condition-dependent quiescent output signals;

a plurality of output circuits each connected to receive the output signal from a different one of said photosensitive devices;

a quiescent output signal monitor device having a condition-dependent quiescent output which is proportional to that of said photosensitive devices;

means for shielding said monitor device from the light to be sensed by said photosensitive devices, whereby the output signal from said monitor device is proportional to the condition-dependent quiescent-output-signal contributions to the output signals from said photosensitive devices; and current mirror means responsive to the output signal from said monitor device for applying condition-dependent-quiescent-output-signal-compensating signals to a plurality of said output circuits to compensate for the condition-dependent quiescent output from each of said photosensitive devices, whereby the output from each of said output circuits is substantially independent of the condition-dependent quiescent output of the one of said photosensitive devices to which it is coupled.

15. The photodetector system recited in claim 14 wherein:

said quiescent output signal is a current.

16. The photodetector system recited in claim 15 wherein:

said monitor device is a different size than at least some of said photosensitive devices; and said current mirror means scales the signal applied to said output circuits in accordance with the relative sizes of said monitor device and said photosensitive devices.

17. The photodetector system recited in claim 15 further comprising:

a second monitor device coupled to said current mirror means in a manner to combine the condition-dependent quiescent currents derived from the first recited and said second monitor devices to more accurately compensate said photosensitive devices of said photodetector system.

18. The photodetector system recited in claim 17 wherein:

said photosensitive devices are arranged in a linear array extending in a first direction and said monitor devices are disposed on opposite sides of said linear array in a second direction disposed at an angle to said first direction.

19. The photodetector system recited in claim 17 wherein:

said photosensitive devices are arranged in a linear array extending in a first direction and said monitor devices are spaced apart and disposed in the vicinity of opposite ends of said linear array.

20. The photodetector system recited in claim 19 wherein:

said monitor devices are disposed on opposite sides of said linear array in a second direction disposed at an angle to said first direction.

21. A photodetector system comprising:

a continuous output photosensitive device which exhibits a condition-dependent quiescent current;

an output circuit connected to receive the output current from said photosensitive device;

a condition-dependent quiescent current monitor device having a condition-dependent-quiescent-current response which is proportional to that of said photosensitive device;

means for shielding said monitor device from the light to be sensed by said photosensitive device, whereby the output of said monitor device is proportional to the condition-dependent-quiescent-current contribution to the output signal from said photosensitive device;

current mirror means responsive to said monitor device for applying a condition-dependent-quiescent-current-signal compensating signal to said output circuit to compensate for the condition-dependent quiescent current from said photosensitive device whereby the output from said output circuit is substantially independent of the condition-dependent quiescent current of said photosensitive device.

22. A current mirror comprising:

an input section including a monitor device and an input control device connected to in a manner in which a reference output signal from said monitor device biases said input control device to provide said output signal;

a plurality of output sections each including:

an output control device, and a compensated device connected to said output control device in a manner corresponding to the connection of said monitor device to said input control device;

said monitor and compensated devices having corresponding characteristics whereby, said current mirror conducts the reference portions of the output signals of said compensated devices.

23. The current mirror recited in claim 22 wherein:

said monitor device reference output signal is a condition-dependent quiescent output signal whereby said current mirror compensates the output circuits of said compensated devices for the condition-dependent-quiescent-output-signal portions of the output signals of said compensated devices.

24. The current mirror recited in claim 23 wherein:

said compensated devices are continuous output devices.

25. The current mirror recited in claim 24 wherein:

said quiescent signal is a current.

26. The current mirror recited in claim 22 wherein:

said monitor device is a different size than at least some of said compensated devices; and said current mirror means scales the signal applied to said output circuits in accordance with the relative sizes of said monitor device and said compensated devices.

27. The current mirror recited in claim 26 wherein: said quiescent signal is a current.

28. The current mirror recited in claim 22 wherein: said monitor device is a different size than at least some of said compensated devices;

not all of said compensated devices are the same size; and said current mirror means scales the signal applied to said output circuits in accordance with the relative sizes of said monitor device and said compensated devices.

29. The current mirror recited in claim 28 wherein: said quiescent signal is a current.

30. The current mirror recited in claim 22 further comprising:

a second monitor device coupled to said current mirror means in a manner to combine the condition-dependent quiescent output signals derived from the first recited and said second monitor devices to more accurately compensate said compensated devices.

* * * * *